(12) United States Patent
Shah et al.

(10) Patent No.: US 10,231,736 B2
(45) Date of Patent: Mar. 19, 2019

(54) SYSTEM AND METHOD FOR SOFT TISSUE GRIPPING

(71) Applicant: The Regents of the University of California, Oakland, CA (US)

(72) Inventors: Sameer B. Shah, San Diego, CA (US);
Johnathan L. Le, Fontana, CA (US);
Daniel Moskowitz, Los Osos, CA (US);
Fabian Ramirez, Modesto, CA (US);
Aileen Tran, West Covina, CA (US);
Nathan Delson, San Diego, CA (US)

(73) Assignees: THE REGENTS OF THE UNIVERSITY OF CALIFORNIA, Oakland, CA (US); THE UNITED STATES OF AMERICA, Washington, DC (US)

(*) Notice: Subject to any disclaimer, the term of this patent is extended or adjusted under 35 U.S.C. 154(b) by 195 days.

(21) Appl. No.: 15/181,287

(22) Filed: Jun. 13, 2016

(65) Prior Publication Data
US 2016/0361064 A1 Dec. 15, 2016

Related U.S. Application Data

(60) Provisional application No. 62/174,439, filed on Jun. 11, 2015.

(51) Int. Cl.
*A61B 17/11* (2006.01)
*A61B 90/00* (2016.01)
*A61N 1/05* (2006.01)

(52) U.S. Cl.
CPC ........... *A61B 17/1128* (2013.01); *A61B 17/11* (2013.01); *A61B 17/1146* (2013.01); *A61B 90/02* (2016.02);
(Continued)

(58) Field of Classification Search
CPC . A61B 17/11; A61B 17/1128; A61B 17/1146; A61B 2017/1103;
(Continued)

(56) References Cited

U.S. PATENT DOCUMENTS 4,602,624 A 7/1986 Naples et al.
4,641,636 A * 2/1987 Cotrel ................ A61B 17/7049
606/250

(Continued)

FOREIGN PATENT DOCUMENTS

CA 2333121 A1 11/1999
CA 2266999 A1 9/2000
(Continued)

OTHER PUBLICATIONS

Korvink, J. (2006). Tissue Repair. In MEMS a practical guide to design, analysis, and applications (pp. 739-742). Norwich, NY: W. Andrew Pub., Biomedical Systems, Lye, Reed (4 pages total).
(Continued)

*Primary Examiner* — Robert Lynch
(74) *Attorney, Agent, or Firm* — Stuart H. Mayer; Mayer & Williams PC

(57) ABSTRACT

Systems and methods disclosed stimulate nerve growth by applying a tensile (axial pulling) load on a proximal stump of the nerve. This load may be imposed once, at the time of repair. This implementation may be advantageously employed to remove tension away from the repair site, for any number of soft tissues, e.g., nerves, ligaments, tendons, and so on. Alternately, for a larger gap, by progressively elongating a nerve through tensile stimulation, the nerve may regenerate and be fully functional, particularly if elongated at a proper rate. After sufficient regrowth, nerve ends may be reattached, resulting in more complete functional recovery. Two implementations, which have been embodied
(Continued)

BREAKDOWN OF NERVE REPAIR PROCESS in prototype devices, also include particularly useful features, one of which uses a screw and clamp with slotted insert design, and the other of which enables the use of sutures or straps to secure the tissue to the clamp.

21 Claims, 18 Drawing Sheets

(52) U.S. Cl.
CPC ............ *A61B 2017/1103* (2013.01); *A61B 2017/1132* (2013.01); *A61N 1/05* (2013.01); *A61N 1/0556* (2013.01); *A61N 1/0558* (2013.01)

(58) Field of Classification Search
CPC ... A61B 2017/1132; A61B 90/02; A61N 1/05; A61N 1/0556; A61N 1/0558
See application file for complete search history.

(56) References Cited

U.S. PATENT DOCUMENTS

| | | | |
|---|---|---|---|
| 5,342,376 A | | 8/1994 | Ruff |
| 5,464,414 A | * | 11/1995 | Cziffer ............... A61B 17/1128 606/150 |
| 5,800,544 A | * | 9/1998 | Demopulos ........ A61B 17/1146 606/53 |
| 5,919,220 A | | 7/1999 | Stieglitz et al. |
| 6,106,556 A | * | 8/2000 | Demopulos ........ A61B 17/1146 606/323 |
| 6,547,783 B1 | | 4/2003 | Vilendrer et al. |
| 8,116,882 B2 | | 2/2012 | Kowalczewski |
| 8,214,056 B2 | | 7/2012 | Hoffer et al. |
| 2003/0040785 A1 | | 2/2003 | Maschino et al. |
| 2006/0030919 A1 | | 2/2006 | Mrva et al. |
| 2010/0331883 A1 | * | 12/2010 | Schmitz ............. A61B 10/0275 606/249 |
| 2012/0289800 A1 | | 11/2012 | Isaacson et al. |
| 2014/0228867 A1 | | 8/2014 | Thomas et al. |

FOREIGN PATENT DOCUMENTS

| | | |
|---|---|---|
| CA | 2554574 A1 | 8/2005 |
| EP | 2 556 799 A1 | 2/2013 |
| WO | 2000035530 A1 | 6/2000 |

OTHER PUBLICATIONS

Romero E, Denef JF, Delbeke J, Robert A, Veraart C., "Neural morphological effects of long-term implantation of the self-sizing spiral cuff nerve electrode" Med Biol Eng Comput. Jan. 2001; 39 (1): 90-100. (11 pages total).

Slot, P.J., Selmar, P., Rasmussen, A., and Sinkjaer, T. (1997). "Effect of long-term implanted nerve cuff electrodes on the electrophysiological properties of human sensory nerves" Artificial Organs 21(3), 207-209. (3 pages total).

Johnathan Le, et al., "A Nerve Gripping Device for Nerve Repair" Departments of Orthopaedic Surgery & Bioengineering, UC San Diego School of Medicine (Poster Presentation) Jun. 11, 2015.

Johnathan Le, et al., "Nerve Gripping Mechanism" Department of Mechanical and Aerospace Engineering, Jacobs School of Engineering at UC San Diego, Spring 2015 (67 pages total).

* cited by examiner

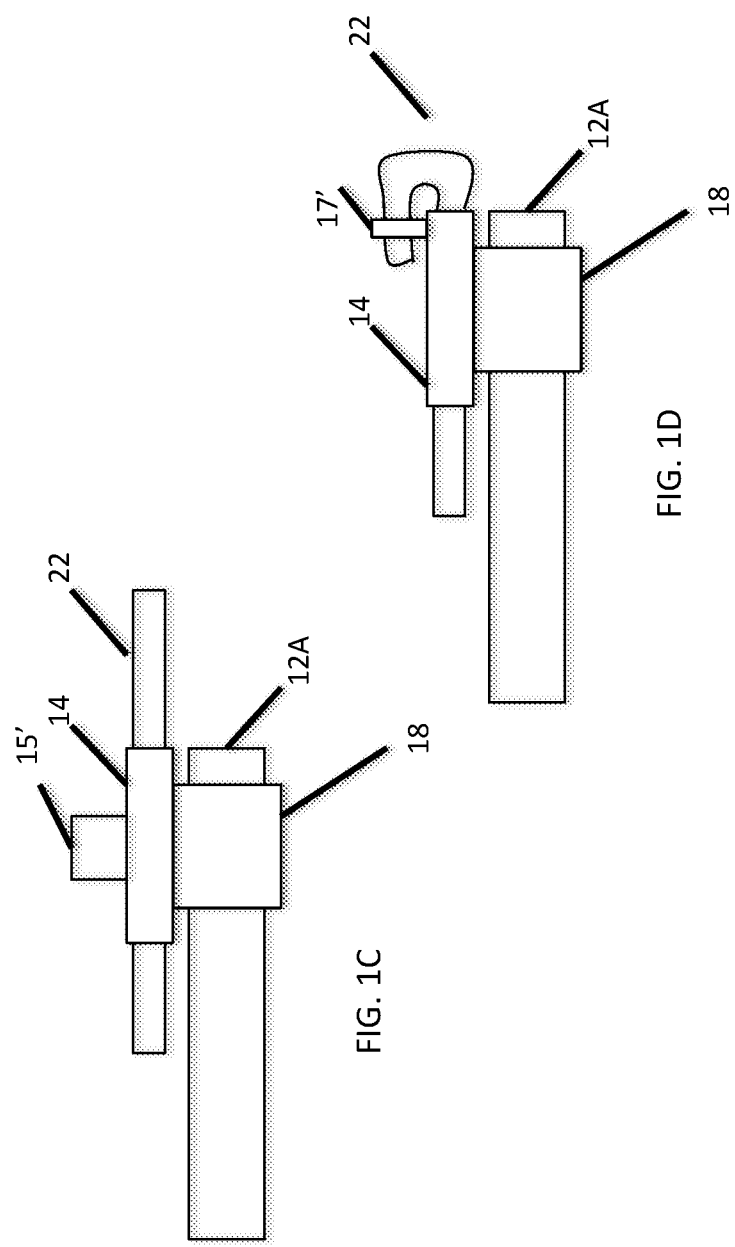

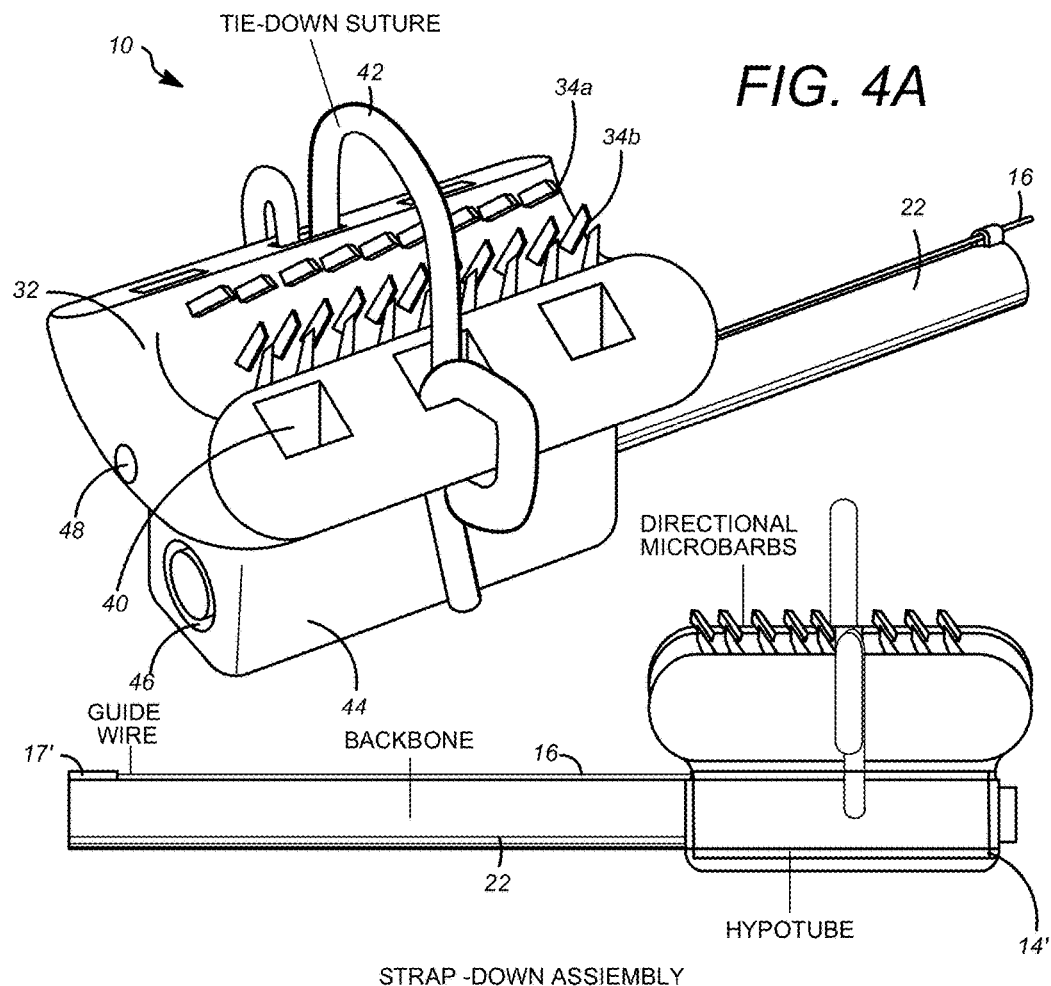

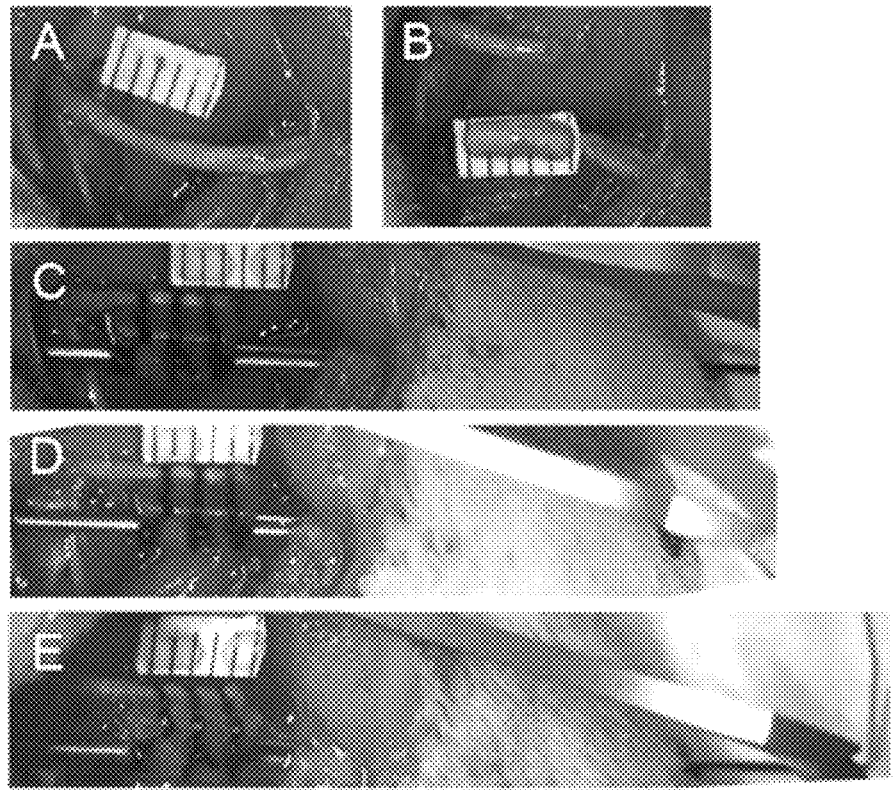

A. Exposed rat sciatic nerve, pre-operative.
B. 5mm nerve gap imposed.
C. Nerve lengthening device implanted, using nerve gripping technology to interface with nerve.
D. Nerve lengthened ~4mm with an external guidewire that is connected to clamp/device (superphysiological stretch, no device slippage).
E. Nerve lengthened ~6+ mm with same guidewire. There is no slippage of device from nerve, despite considerable shear and tension in nerve at this superphysiological stretch.

FIG. 12

SYSTEM AND METHOD FOR SOFT TISSUE GRIPPING

CROSS-REFERENCE TO RELATED APPLICATIONS

This application claims benefit of priority of U.S. Provisional Patent Application Ser. No. 62/174,439, filed Jun. 11, 2015, entitled "SOFT TISSUE GRIPPING DEVICE", owned by the assignee of the present application and herein incorporated by reference in its entirety.

GOVERNMENT FUNDING

This invention was made with government support under Project No. B1471-R/Award# IRX001471A awarded by the Veterans Administration. The government has certain rights in the invention.

FIELD

The invention relates to devices for gripping soft tissue.

BACKGROUND

Peripheral nerve damage is a serious and rising concern, and affects up to 1% of the US population by age 70. Typical causes include traumatic injury, vehicular accidents, sports injuries, wartime injuries and repetitive stress. Consequences of peripheral nerve damage include loss of mobility, motor function and sensation, and severe pain, among others.

In many cases, nerve damage manifests itself as a severed nerve, between a proximal end, which is close to the spinal cord, and which is "live", separated from a distal end, which is distant from the spinal cord, and degenerating. Gaps may exist of various sizes, and a large gap may be one that is over 10 mm. If contact between the proximal and distal ends of the nerve can be achieved, nerve axons can regrow, resulting in recovery of the nerve.

Every year, approximately 50,000 nerve repair procedures are performed in the United States. Nevertheless, few if any effective strategies exist to repair large gaps. The most common technique is to graft a portion of a nerve from a cadaver or a nerve fragment from elsewhere in the patient's body into the space between the detached nerve ends. These solutions are not always successful, and have limitations. Another concept that has been proposed is to lengthen the nerve, bringing proximal and distal ends closer together. In one exemplary technique, a balloon is used whose expansion extends a nerve, but such techniques "bow" the nerve nonlinearly, with undesired results. In another technique, a large device is employed to secure nerve ends. This device is disadvantageous though, as the patient is rendered essentially immobile.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

Systems and methods according to present principles meet the needs of the above in several ways. In particular, systems and methods stimulate nerve growth by applying a tensile (axial pulling) load on a proximal stump of the nerve. This load may be imposed once, at the time of repair. This implementation may be advantageously employed to remove tension away from the repair site, for any number of soft tissues, e.g., nerves, ligaments, tendons, and so on. Alternately, for a larger gap, by progressively elongating a nerve through tensile stimulation, the nerve may regenerate and be fully functional, particularly if elongated at a proper rate. After sufficient regrowth, nerve ends may be reattached, resulting in more complete functional recovery.

While described below in the context of gripping nerve ends or stumps to stimulate nerve growth, systems and methods according to present principles provide ways to grip any sort of soft tissue without damaging the same. The systems and methods provide in particular clamping mechanisms which were developed to grip peripheral nerves, but the systems and methods may be applied to any number of soft tissues, such as ligaments, tendons, and muscles.

Two implementations, which have been embodied in prototype devices, also include particularly useful features, one of which uses a screw and clamp with slotted insert design, and the other of which enables the use of sutures or straps to secure the tissue to the clamp.

The first implementation of the device incorporates a two-part clamp that uses a single screw as its tightening mechanism. To assist with the alignment of the two parts and screw, a slotted male-to-female insert may be used. The nerve is placed between the top and bottom parts of the clamp, and then the screw is fastened to secure an effective grip on the nerve.

The second implementation of the device is similar to that of an ambulance gurney. There exists a channel for the nerve to lie on, and then, using straps, the nerve is strapped down to the channel. The straps are threaded radially along the channel through fabricated slots.

Both strategies may enlist the use of directional surface piercing elements (micro-barbs) to assist in the attachment strength to the nerve. These elements pierce the outer layer of the tissue (for a nerve, the epineurium), preventing the devices from slipping off the nerve when being pulled during the nerve lengthening process, but protecting the underlying active neural elements below the epineurium. The directional micro-barbs are oriented such that the piercing heads are opposing the direction of nerve elongation, similar to how a hose barb fitting works. The directionality of the microbarbs may in some cases be a particularly unique feature.

The devices are modular and can be readily scaled, and materials altered, depending on the scale and material properties of the tissue clamped. Unlike previous tissue gripping devices, devices according to present principles in some implementations may be microfabricated, allowing flexible material choice.

Devices according to present principles may be manufactured with bio-compatible materials and may be configured to be small enough to fit within a nerve injury setting of the body. The device may be designed with a backbone system to use in a nerve lengthening process. During this process, the device is pulled, and the device is designed to securely grip the nerve such that is does not slip off when being pulled or tugged.

Systems and methods according to present principles may be employed in neurosurgical or orthopedic applications for soft tissue repair, following acute traumatic injury or chronic degenerative injury. The modularity also lends itself to customizing device geometry and scale, for varied tissue dimensions. The targeted patients who would benefit from this device include those from military or veteran populations but also traumatic and degenerative injury patients in the general population, for example athletes and the elderly.

In one aspect, the invention is directed towards a device operable to grip tissue, including: a housing; a device connection portion coupled to or defined within the housing; and a tissue engagement portion attached to or defined in the housing, the tissue engagement portion including a tissue engagement surface, the tissue engagement surface having at least one tissue piercing element thereon, the tissue piercing element operable to hold tissue against movement.

Implementations of the invention may include one or more of the following. The device connection portion may define a connection throughhole, the connection throughhole having a cylindrical shape.

The connection through hole may be operable to receive tube, e.g., a hypo tube, and/or a backbone. For example, the backbone may pass through the hypo tube. The hypo tube may be secured in the connection through hole by a friction fit. The backbone may define a slot operable to receive a guidewire.

The housing may further define a guidewire hole, the guidewire hole having a cylindrical shape, and an axis of the cylindrical shape of the guidewire hole may be substantially parallel to an axis of the cylindrical shape of the connection throughhole. The tissue engagement portion may further include at least one suture throughhole, the suture throughhole operable to allow an operator to suture or strap a subject tissue to the tissue engagement surface. The tissue engagement portion may further include a top housing portion and a bottom housing portion, the top housing portion coupled to the bottom housing portion by a tightenable connector, a volume between the top housing portion and the bottom housing portion defining a receiving volume operable to receive tissue to be gripped, and where the at least one tissue piercing element is situated to extend into the receiving volume.

The tissue piercing element may be a micro-barb, and the micro-barb may be operable to engage only an epineurium of a nerve. The device connection portion and the tissue engagement portion may be on opposite sides of the housing.

In another aspect, the invention is directed towards a kit for elongating tissue, including: at least two devices according to the above, a backbone operable to connect via at least two devices and to maintain the at least two devices in sliding engagement, and a means to maintain the at least two devices at a maximum distance.

Implementations of the invention may include one or more of the following. The means to maintain may include a guidewire. The means to maintain may include a set screw operable to hold each of the respective devices against movement relative to the guidewire.

The means to maintain may include a tie off hitch operable to hold each of the respective devices against movement relative to the guidewire.

The elements of the kit may be configured to fit and be implanted within a host.

In another aspect, the invention is directed towards a method for elongating a tissue, or to bring to disparate tissues together, including: attaching a first device according to claim 1 to a proximal portion of tissue; attaching a second device according to claim 1 to a distal portion of tissue; affixing a backbone between the first and second devices, such that a distance between the proximal portion of tissue and the distal portion of tissue is maintained; and successively altering the position of the first or second device, or both, on the backbone, such that the distance is reduced with each successive altering.

Implementations of the invention may include one or more of the following. The affixing a backbone such that a distance is maintained may be performed by maintaining a maximum distance between the proximal portion of tissue and the distal portion of tissue.

Advantages of the invention may include, in certain embodiments, one or more of the following. Systems and methods according to present principles may be employed for securely gripping tissue, while causing little or no damage to the tissue, either electrical damage or mechanical damage. In the case of nerves, the same may be lengthened under axial tension without over compressing or damaging the nerve. Systems according to present principles may be effectively implanted in a patient, and manually pulled at regular intervals, resulting in effective nerve mechanical stimulation and growth. Other advantages will be understood from the description that follows, including the figures and claims.

This Summary is provided to introduce a selection of concepts in a simplified form. The concepts are further described in the Detailed Description section. Elements or steps other than those described in this Summary are possible, and no element or step is necessarily required. This Summary is not intended to identify key features or essential features of the claimed subject matter, nor is it intended for use as an aid in determining the scope of the claimed subject matter. The claimed subject matter is not limited to implementations that solve any or all disadvantages noted in any part of this disclosure.

BRIEF DESCRIPTION OF THE DRAWINGS

FIG. 1C illustrates an exemplary set screw, and FIG. 1D illustrates and exemplary tie-off hitch.

FIGS. 4A and 4B are views of the first implementation of the device in use with a backbone.

FIG. 12 illustrates a prototype of the first implementation of the device in an application of nerve lengthening in a rat.

Like reference numerals refer to like elements throughout. Elements are not to scale unless otherwise noted.

DETAILED DESCRIPTION

Figure 1A:
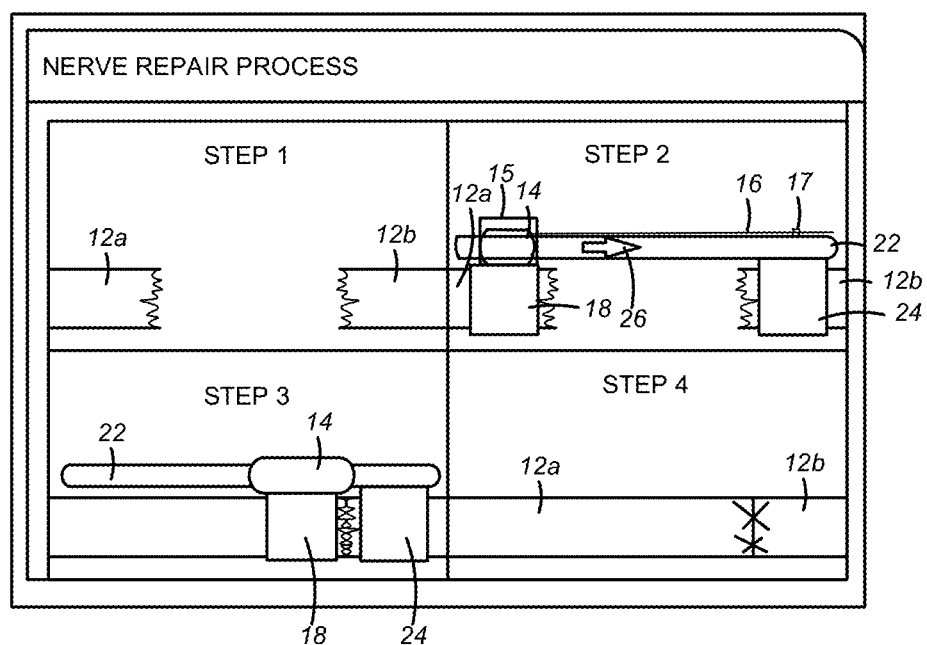
FIG. 1A shows a schematic depiction of a first implementation of devices and methods according to present principles.

FIG. 1A illustrates steps in an exemplary nerve repair process according to present principles. Step 1 shows a proximal stump 12Aa separated from a distal stump 12B. Such nerves may represent, e.g., a severed nerve with a large gap distance (greater than 10 mm) between the ends.

In step 2, a proximal tissue gripping device 18 has been attached to the proximal stump 12A, and a distal tissue gripping device 24 has been attached to the distal stump 12B. The tissue gripping device 24 may include a portion 15 in which a tube 14 is inserted via a friction fit. The tube 14 may have slidably inserted therein a backbone 22. The tube 14 may be, e.g., a hypotube, e.g., high precision tube, or the like. The backbone 22 may be, e.g., a stainless steel rod, although other materials may be used, e.g., titanium or a polymer. Details of the tissue gripping devices are described below.

Figure 1B:
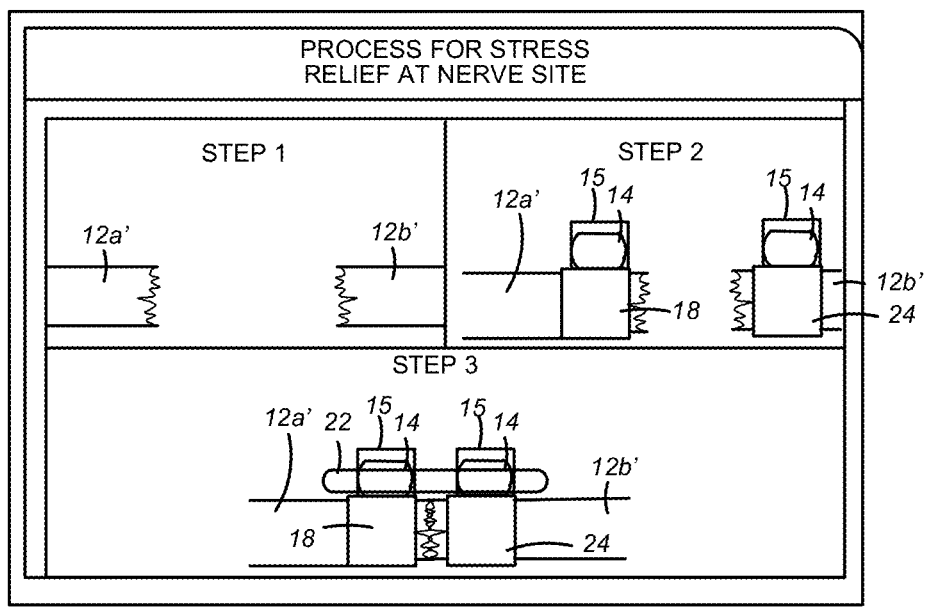
FIG. 1B shows a schematic depiction of a second implementation of devices and methods according to present principles.

As indicated in step 3, the tube 14 may be moved along the backbone 22 in the direction indicated by arrow 26, thus bringing the nerve stumps together. It is noted that FIG. 1 is schematic in nature, to show an exemplary process, and that generally each tissue gripping device will have a tube 14 and a portion 15 (see, e.g., FIG. 1B) moving along the backbone, such that the tissue gripping devices may move relative to each other.

The stump may be moved in this direction by retraction of a guidewire 16 which is attached to the tube 14 and threaded through a slot 17 associated with the tissue gripping device 24.

In one implementation, nerve growth may be stimulated by the device such that the nerve experiences a certain percentage elongation each day. Eventually, as indicated by step 4, the proximal nerve stump reaches the distal nerve stump. In one implementation, for example, three weeks of stimulation and nerve growth were needed to bring the severed ends together, with sequential extensions performed every few days. At this point, the device may be removed, and the ends physically attached, e.g., by suture. It is noted in this regard that, in the case of joining nerve ends, the proximal nerve end is generally moved closer to the distal nerve end, as opposed to moving the distal nerve end, as moving the proximal and can stimulate nerve growth, as opposed to the distal end, which lacks living cells, but which can still provide a useful scaffold for the growth of new nerve cells.

As will be described in greater detail below, exemplary components of the device include the backbone rod 22, the tubes 14, tissue gripping devices 18 and 24, as well as the guidewire 16.

An alternate exemplary repair process is shown in FIG. 1B, for a more modest gap (step 1) that is not readily repaired by pulling nerve stumps 12a' and 12b' together, due to tension at the repair site. In this implementation, devices 18 and 24 are attached to proximal stump 12a' and distal stump 12b', respectively (step 2). The stumps are brought together at the time of repair, and the devices connected such that the stumps may be sutured together without tension at the site of reconnection (step 3). Devices may be connected using a backbone 22 as for FIG. 1A or using surgical suture (see also the example implementation in FIG. 13).

Functional requirements of certain implementations may include one or more of the following. The device should be configured to reliably clamp onto a nerve or other target tissue. The device should be configured to not excessively compress the nerve or other tissue. The device should be configured to distribute a radial compressive load along the nerve or other tissue. The device should be configured to secure to a lengthening system. The device should be manufactured with biocompatible materials. The device should be configured to fit within the nerve injury setting, in vivo (or other target tissue setting).

First Implementation—"Strap Down" Design

Figure 2:
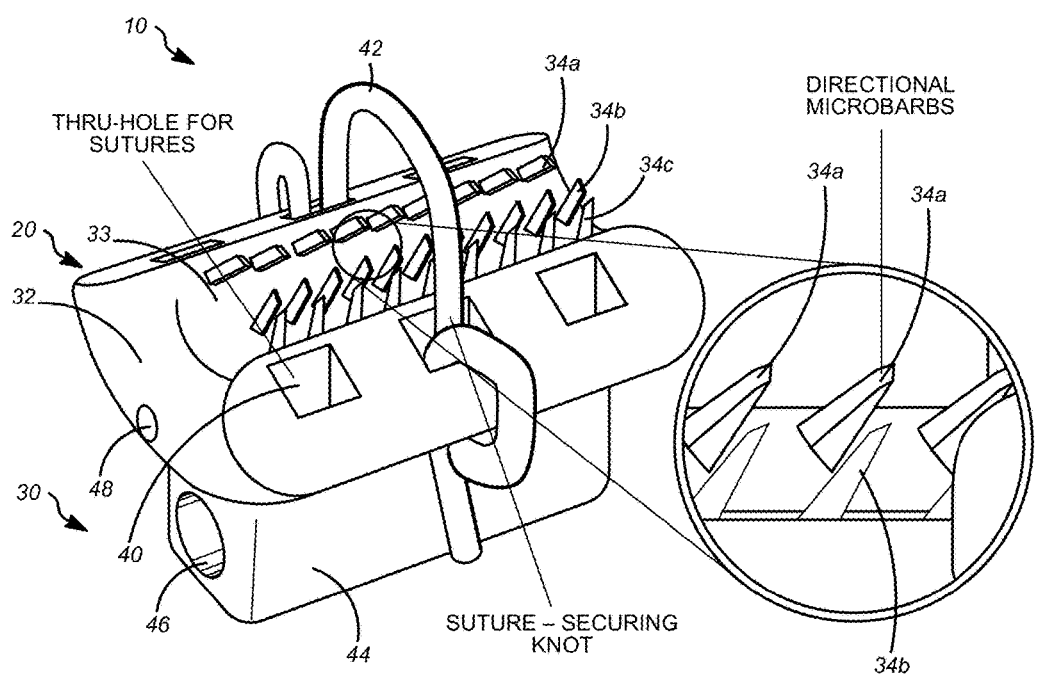
FIG. 2 is a perspective view of a first implementation of a device according to present principles.

FIG. 2 illustrates a first exemplary implementation of a device 10 according to present principles, this implementation termed a "strap-down design", as the same has capability for suture-induced compression of the tissue on the clamp channel. The device 10 may be seen to include a housing 44 having a device connection portion 30 coupled thereto, the device connection portion including, e.g., a device connection throughhole channel 46 for the tube 14 to pass through. The backbone than passes through the tube. Generally each tissue gripping device will define a device connection throughhole in which a hypotube or the like may be placed, and in which a backbone rod may be inserted in a slidable fashion. In many cases the connection throughhole has a cylindrical shape and an associated axis, as does the tube, e.g., hypotube.

The device 10 further includes a tissue engagement portion 20, the tissue engagement portion including, e.g., a tissue engagement surface such as an arcuate wall 32 coupled to the housing 44, the arcuate wall generally configured to receive a subject tissue, e.g., a nerve. The arcuate wall may have an interior face 33 on which a number of tissue piercing elements such as micro-barbs 34a, 34b, and 34c are situated. In the implementation of FIG. 2, the micro-barbs are illustrated in three rows or lines, the lines parallel to the length of the arcuate wall 32. Details of the micro-barbs 34a, 34b, and 34c are described in greater detail below, but it is noted here that the same may be preferably angled, such that the same are pointing in a direction opposite to that to which force is being applied. In this way, the micro-barbs effectively hold the tissue against movement. The micro-barbs dig into the nerve outer layer, securing the nerve to the device through increased friction.

One or more suture throughholes 40 are defined within the arcuate wall 32, the same for passage of a suture 42 to affix the soft tissue to the arcuate wall and to the micro-barbs 34a-34c. While the implementation of FIG. 2 shows three suture throughholes 40, more or less may be provided as needed to secure tissue. The number of throughholes is generally determined by the size of the tissue to be secured, whether the tissue is slippery, and other similar factors.

In this implementation, the nerve is strapped down by a number of sutures, similar to a shoelace or gurney. The suture may be threaded through the holes prior to the surgery or other procedure, and the sutures may then be tightened around the nerve during surgery.

A guidewire hole 48 may be situated within the arcuate wall 32 to allow passage of a guidewire through the tissue gripping device 10. While it has been found useful to situate the guidewire hole 48 as near as possible to the nerve, so as to move the actuation axis closer to the nerve axis (and thus reduce the shear force on the nerve), the guidewire may also pass through the device connection throughhole 46 or even outside of the device, e.g., exterior of the housing 44. In the case of FIG. 2, such a guidewire may pass underneath the device shown. However, another benefit of providing the guidewire hole 48 is that use of such constrains the rotational degree of freedom of one device relative to another, and thus the use of two holes 46 and 48 helps to align the devices such that the same are close to being in a line, as opposed to being rotated about the axis of the backbone/tube.

In one implementation built, the design fits completely into a 4 mm×5 mm×6 mm box.

Second Implementation—"Screw Clamp" Design

Figure 3A:
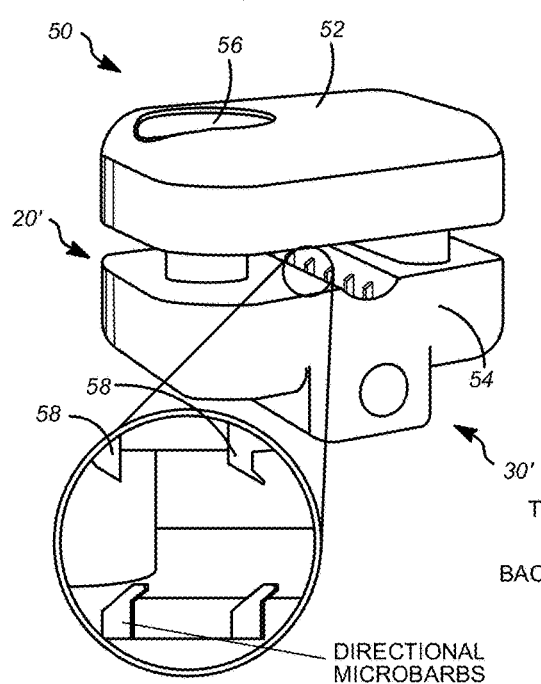
FIGS. 3A and 3B are views of a second implementation of a device according to present principles.
Figure 3B:
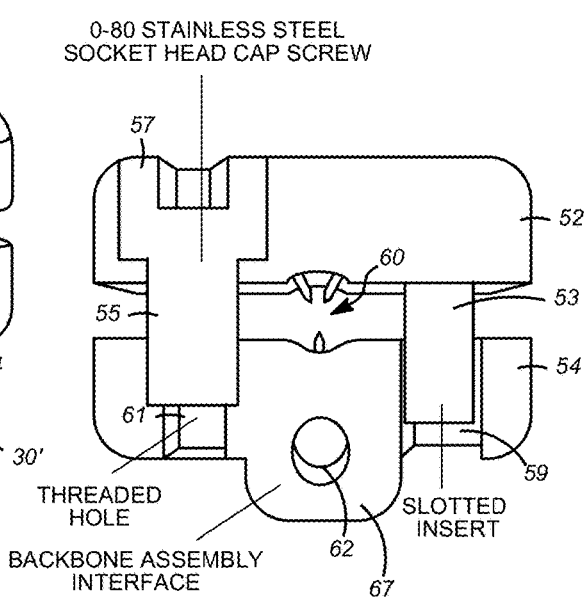

FIGS. 3A and 3B illustrate a second implementation of a device according to present principles. This device includes a housing including a tissue engagement portion 20' and a device connection portion 30'. In both implementations, the tissue engagement portion may be generally on the side of the housing opposite that of the device connection portion, although this is not a requirement and the location of one relative to the other may vary.

In FIGS. 3A and 3B, the device 50 is termed a "screw clamp design", and the same includes a top housing portion 52 which couples to a bottom housing portion 54. A tight-enable connector such as a screw 57 connects the top housing portion 52 with the bottom housing portion 54, the screw 57 passing through a throughhole 56 in the top housing portion and being tightened into a threaded hole 61 in the bottom housing portion 54. For stability, an insert 53 may be inserted into a slot 59 defined in the bottom housing portion 54, such that the top housing portion 52 is coupled to the bottom housing portion 54 in a stable manner, and to prevent rotation.

A nerve to be gripped (or other such tissue) is placed within a receiving volume 60 defined by the top housing portion 52 and the bottom housing portion 54. Tissue piercing elements such as micro-barbs 58 are illustrated that penetrate into the receiving volume 60 and which securely attach to the nerve or other tissue. A section of the bottom housing portion 54 is defined as a backbone assembly interface 67, and the backbone, e.g., backbone 22, may pass through the hole 62 defined in the interface 67, also termed a guide channel for hypotube/backbone placement. The screw 57 with shank 55 is then tightened to move the top portion 52 towards the bottom housing portion 54.

Generally one screw or other such fastener is required to be tightened for a convenient user interface. As with the implementation of FIG. 3, three rows of directional micro-barbs may be employed to increase friction on nerve surfaces. In one implementation, the dimensions of the device are 5×7×5 mm.

In either case, the devices may be packaged as a kit, e.g., with one, two, or more tissue gripping devices, a backbone rod, one or more hypotubes, sutures, set screws, screwdrivers, and so on.

In any given implementation, and as illustrated in FIG. 1, where two tissue gripping devices are employed to secure two portions of tissue in a relative position and/or orientation, such as to eventually bring the two together for fusion or other purposes, the two tissue gripping devices may be coupled by a backbone. The backbone may be secured to one on a permanent basis, and secured to the other on an impermanent basis, or the backbone may be secured to each of the two tissue gripping devices on an impermanent basis. Securement on an impermanent basis may include, e.g., receiving the backbone in a tube 14 or in a hole defined in the tissue gripping portion, e.g., hole 62 or hole 46. As noted in FIG. 1, it is been found convenient to secure the backbone in the hypotube 14, such as by selection of dimensions to allow telescoping of the tube 14 over the backbone, or anchoring via the guidewire 16, which is secured to the hypotube 14. The guidewire 16 may then pass through a slot 17 in the other tissue gripping device, or may pass through a hole 48 defined in the tissue gripping device (see FIG. 2) as described, with accompanying benefits. The guidewire may be "tied off" or bent to maintain a desired maximum distance between the tissue gripping devices, as may be desired in the case where severed nerve endings or stumps are being brought together and joined. In other implementations, a set screw 15' may be employed to secure the wire against movement(see FIG. 1C). Other techniques may also be used, e.g., a tie off hitch 17' using which the guidewire may be secured (see FIG. 1D).

The hypotube, also termed a hypotube insert, may be 3-D printed to allow for ease of insertion and attachment to a tissue gripping device. The clearance may allow for positioning of the clamp and the hypotube. An exemplary hypotube may have a length of, e.g., 3 mm. This sizing ensures sufficient attachment and coupling of the hypotube and the tissue gripping device, and does not increase the overall size of the gripping device.

The size of the overall system or assembly including the two tissue gripping devices, backbone, and accompanying equipment, is such that the same may be implanted in a patient, allowing the patient significant mobility. This may be contrasted with prior ways of joining nerves in which the patient was required to be stationary.

FIGS. 4A and 4B illustrates a tissue gripping device of the strapdown variety in use with a backbone and guidewire. A hypotube 14' is illustrated within the tissue gripping device, and the same secures the tissue gripping device to the backbone. A guidewire 16 is attached to the hypotube, and the same extends through a slot 17' on the backbone. It will be understood that, where two devices are employed, the guidewire may extend through a corresponding slot or hole on the other tissue gripping device, and that the slot 17' on the backbone is optional. The direction of the pulling force on guidewire 16 is generally away from the device 10.

Figures 5A, 5B:
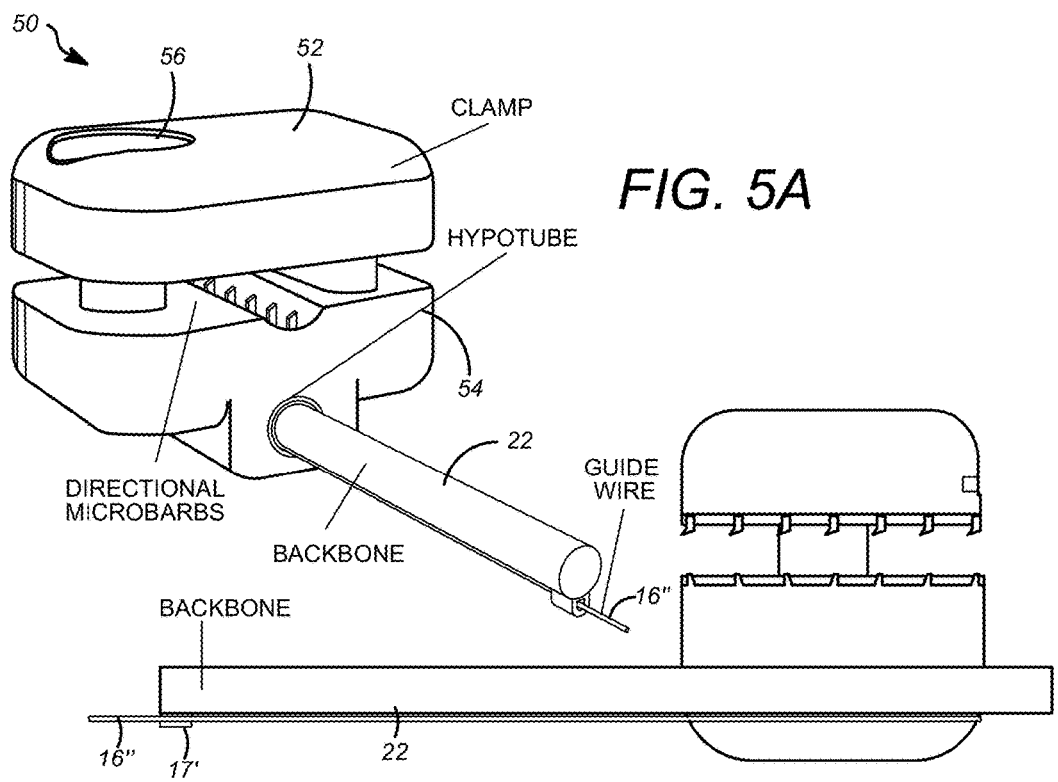
FIGS. 5A and 5B are views of the second implementation of the device in use with a backbone.

FIGS. 5A and 5B illustrates a tissue gripping device of the screw and clamp variety in use with a backbone 22 and guidewire 16". The direction of the pulling force on guidewire 16" is generally away from the device 50. Certain elements are the same as in FIGS. 4A and 4B, and their description is not repeated.

Micro-Barbs

Figure 6:
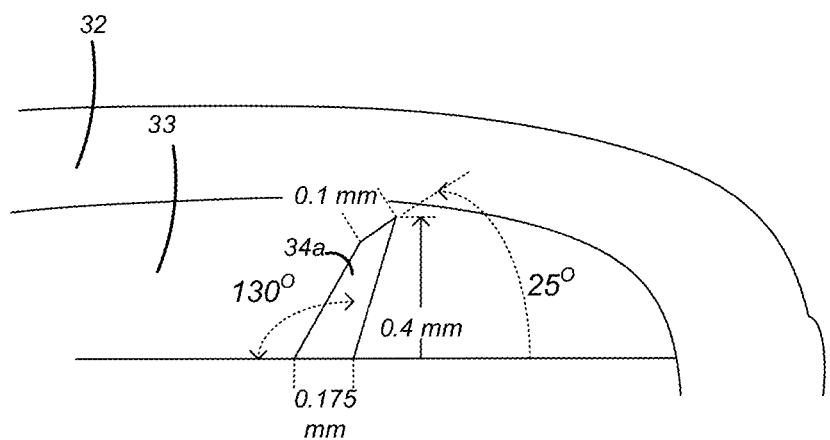
FIG. 6 is a detailed view of a micro barb according to present principles.
Figure 7:
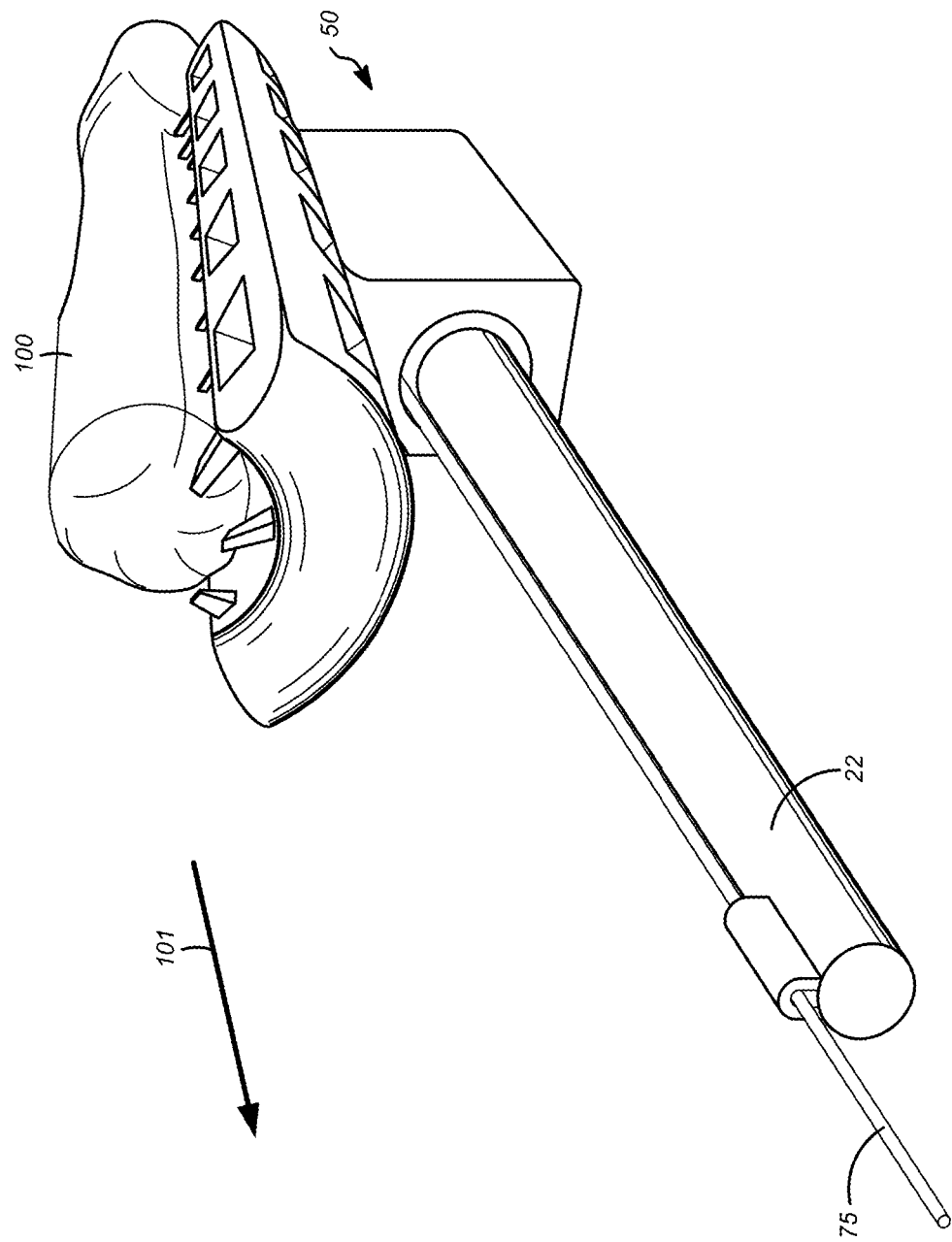
FIG. 7 is a schematic depiction of the first implementation of the device in use with a nerve.

A detail of an exemplary micro-barb is shown in FIG. 6. The effect of the micro-barbs is to increase attachment strength by adding surface piercing elements. The micro-barbs may be directional, with the piercing head oriented to oppose the direction of nerve elongation. In particular, and referring to FIG. 7, tissue 100 is being pulled in a direction shown by arrow 101, and the barbs are in a direction to oppose motion of the tissue opposite to arrow 101.

In one exemplary implementation, the micro-barbs have a square base, of dimensionality 0.175 mm×0.175 mm, and the angle of the barb from the horizontal is 130°. The height of the barb may be, e.g., 0.4 mm, where such represents the distance the barb extends from the surface 33 (with the actual length of the barb being dependent on the angle of directionality).

In another implementation, the square base has a side length of 0.4 mm, and the height may be 0.8 mm. Variations may include one or more of the following. The micro-barbs may be replaced with, e.g., a roughened surface, adhesives, and so on.

The square base may be preferable for stability of the micro-barbs, and the angle of the barbs may be selected such that they can effectively penetrate or hook and hold the tissue against movement. Angles of between 40° and 50° have been found useful, e.g., 45°. If the barbs are too shallow they will not be able to grab the tissue, and if the angle is too great, i.e., an angle closer to perpendicular, the barbs may be caused to break off by the tissue.

Another consideration for the barbs are that the same are desired to penetrate the outer layer of the nerve, i.e., the epineurium. The epineurium provides an outer sheath of an extracellular matrix or a collagenous tissue. No electrical signals propagate in this layer, and so the same is desirable for penetration. Deeper than the epineurium are layers with neurons, and these layers are generally undesirable for penetration. Thus the piercing elements, e.g., micro-barbs, should not generally pierce deeper than 130 μm to prevent damage to the inner nerve.

EXAMPLES

Nerve Lengthening/Elongation for Regrowth

Figure 8:
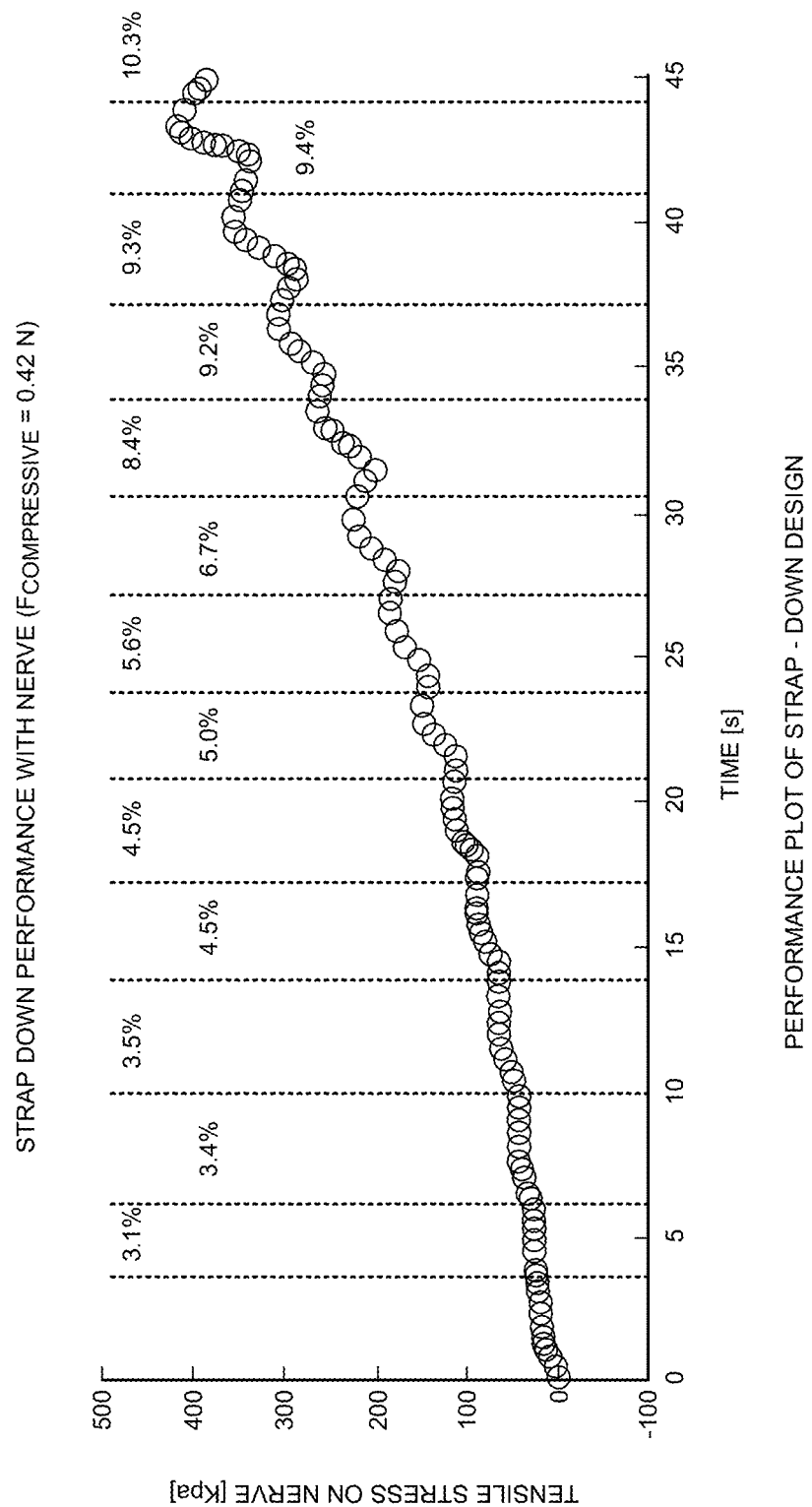
FIG. 8 is a chart illustrating performance of the first implementation of the device.
Figure 9:
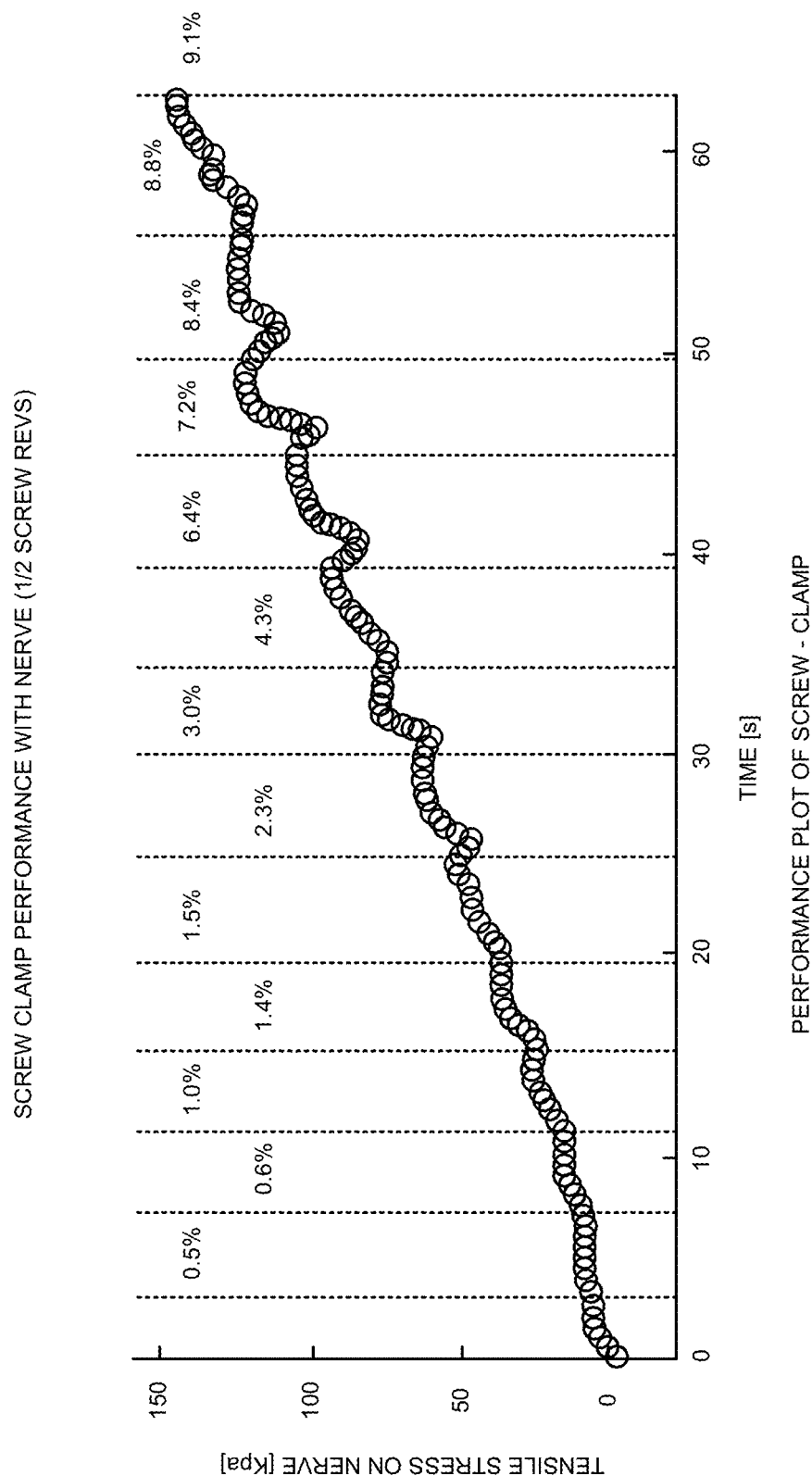
FIG. 9 is a chart illustrating performance of the second implementation of the device.

FIG. 8 and FIG. 9 illustrates performance of the devices, and in particular the performance of the strapdown device (FIG. 8) and the screw clamp device (FIG. 9) in the context of nerve lengthening/elongation. As can be seen, slippage does not occur at the noted compressive forces, and a constant increasing tensile force is seen with elongation.

However, a small oscillation is evident which is caused by stress relaxation. These represent small dips in tensile stress and were observed throughout data collection; the same are attributed to viscoelastic material properties of the nerve (which are similar to those of other soft biological tissues), not device failure. In particular, as each sequential elongation occurs, a peak stress is measured; subsequently, tissue relaxation occurs, reducing the amount of measured stress until the next subsequent elongation. As shown by plots described below, the device was successfully able to securely grip onto rat sciatic nerves and not slip off when being pulled.

The slope increases at later points in time, indicating additional stress after significant elongation. In FIG. 8, a total elongation is seen of 10.3%. In FIG. 9, a total elongation is seen of 9.1%. In this implementation, and comparing with FIG. 10 below, a minimum of between 0.25 and 0.5 screw revolutions is required to ensure proper clamping.

Figure 10:
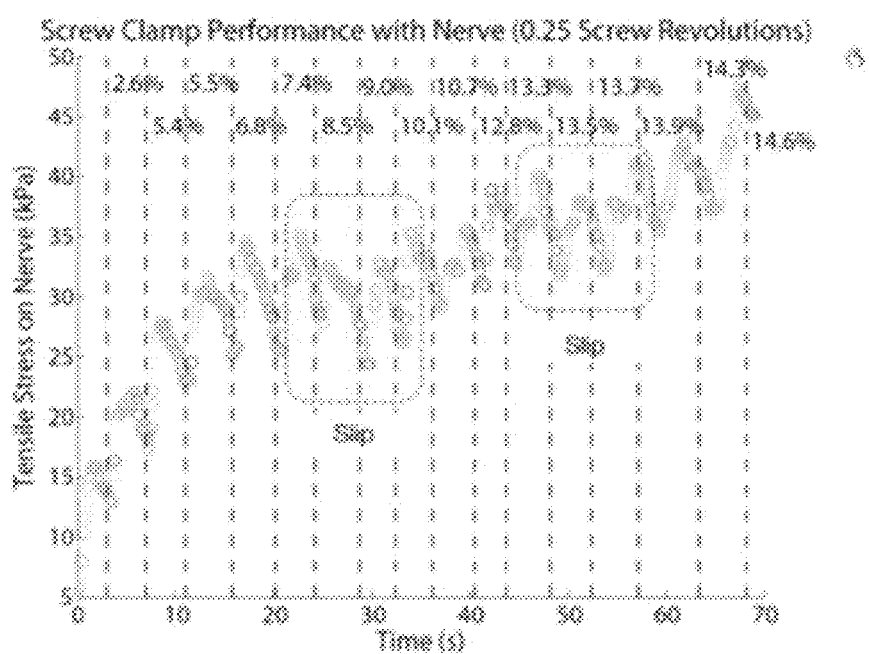
FIG. 10 is a chart illustrating performance of the second implementation of the device, with inadequate tightening leading to tissue slippage.

FIG. 10 illustrates performance of the screw clamp embodiment with less compressive force. As may be seen by the inconsistent trend of the data and the sharp, sudden decreases in tensile stress, the device slipped off the nerve when the nerve was being pulled to 8.5% and 13.5% elongation strain.

Figure 11:
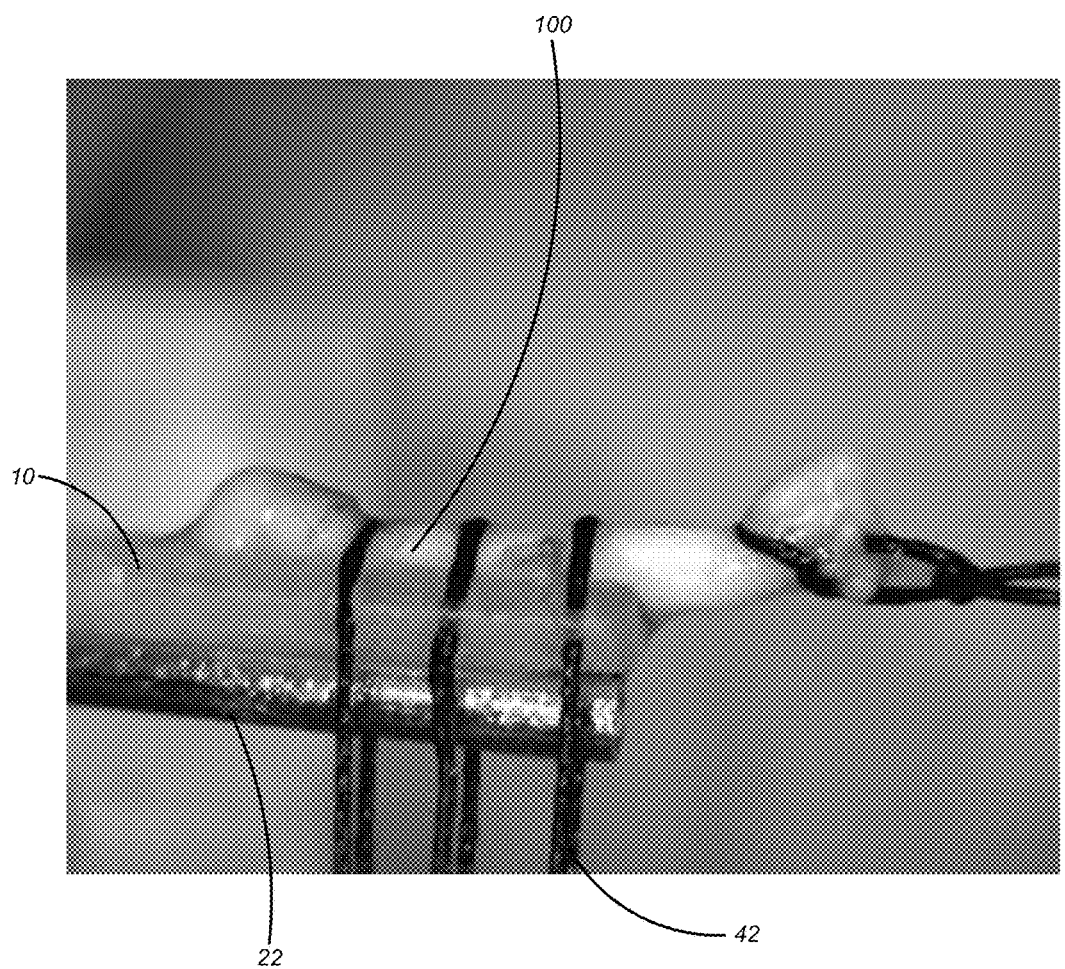
FIG. 11 illustrates a prototype of the first implementation of the device in use with a rat nerve.

The initial practical demonstration of the device was in the context of a nerve lengthening device, for regenerating nerves of the peripheral nervous system. Appropriate clamping allows the device to impose a tensile load to the severed nerve end. This implementation generally uses the device and procedures shown in FIG. 1A, and in a test implementation, the device reliably gripped onto a rat's sciatic nerve without excessively compressing or damaging the nerve. For example, referring to FIG. 11, the same shows an ex vivo demonstration of tissue gripping and extension using a device according to present principles.

In a related embodiment, where sequential elongation is desired, the device may be implanted in the body, but with a temporary port provided, allowing manipulation of a guidewire. In this way, a user may be enabled to bring two tissue gripping devices together in a series of steps. The guidewire and guidewire hole may be configured to have a ratchet feature, to allow guidewire retraction to be the only step necessary to bring the two tissue gripping devices together. Having the guidewire channel separate from the backbone channel allows a preferential angle of rotation to be defined between the devices (and in most cases the devices are desired to not be rotated relative to each other), such that the user can be assured of proper orientation even if manipulating an implanted device via a guidewire, i.e., manipulating a device under the skin that they cannot see.

Referring to FIG. 12, an example is shown for an application of the tissue gripping device for nerve lengthening. In this implementation, a rat sciatic nerve was lengthened superphysiologically, without device slippage. In particular, there was no slippage of the device from the nerve, despite considerable shear and tension in the nerve at this superphysiological stretch. In all images, the scale ruler is subdivided into millimeters in the figures. The proximal device is to the left, and the distal device is to the right. Black elements are sutures, and the tissue gripping devices are translucent. In this example, a nerve was stretched effectively by 6 mm without device slippage.

Figure 13:
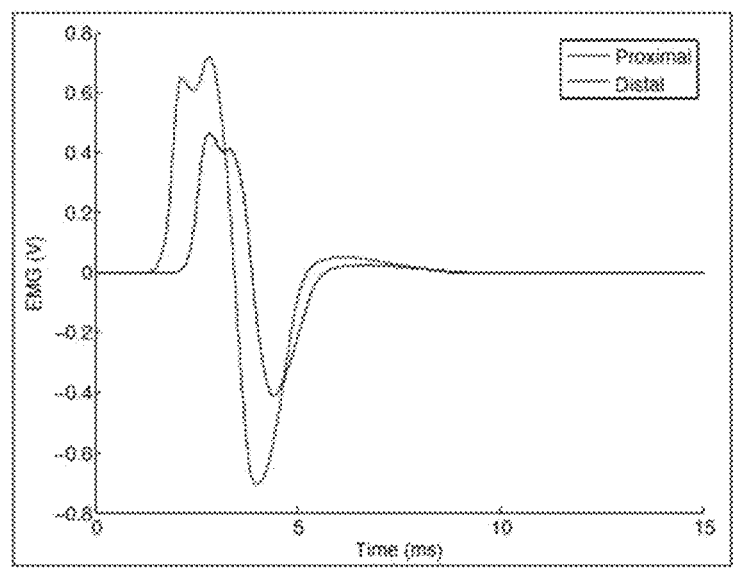
FIGS. 13 and 14 show electromyography results, indicating no electrical damage to nerves used in devices according to present principles.
Figure 14:
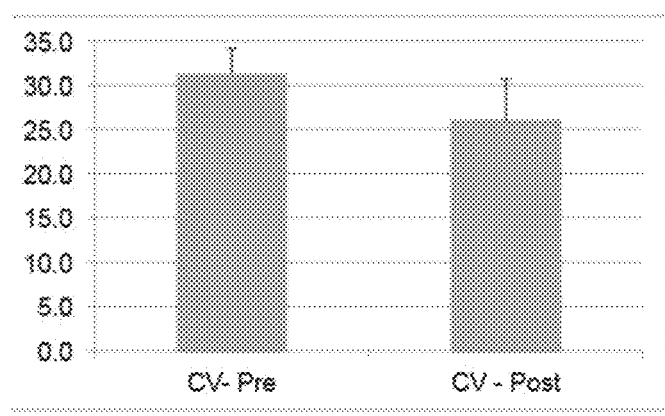

As may be seen in FIG. 13, electromyography testing confirmed that device implantation did not damage nerve conduction in uninjured nerves, suggesting that compression was not substantial. As may be seen from FIG. 14, conduction velocity across the cuffed region is slightly reduced, but not significantly, based on recordings before and after device implantation (n=5).

In another example, experiments showed that the stress and strain on the nerves gripped using devices disclosed here are essentially the same as they were before the nerve was severed, thus indicating no significant mechanical damage is occurring to the nerves, i.e., little to no additional stress is being added to the nerve, as compared to the case of a direct repair.

Non-Lengthening Implementations

Figure 15:
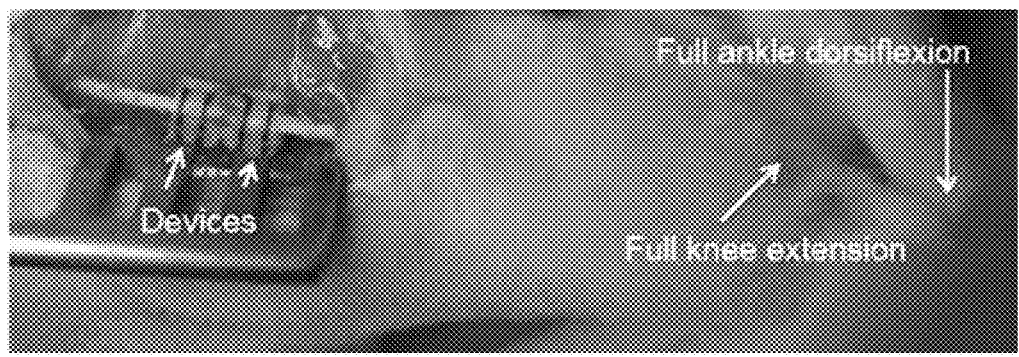
FIG. 15 illustrates a prototype of the implementation of FIGS. 11A-11D in an application of strain relief in a rat.
Figure 16A:
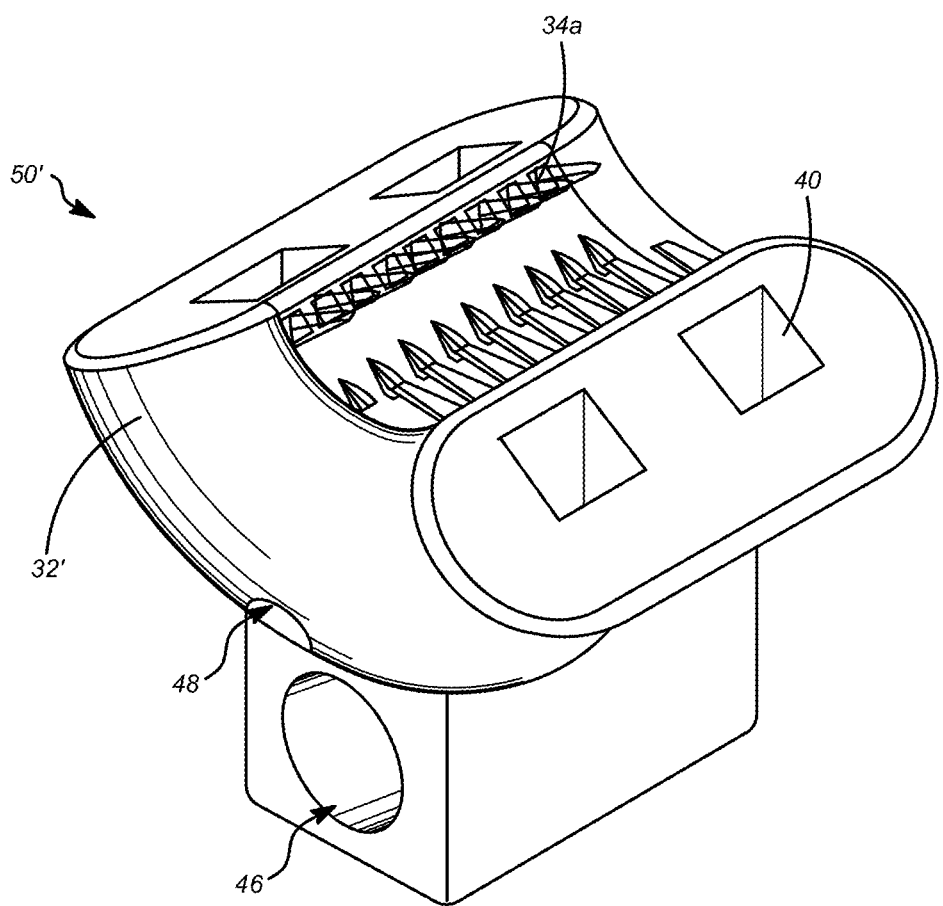
FIGS. 16A-16D illustrate an alternative size version of the first implementation of the device.
Figure 16B:
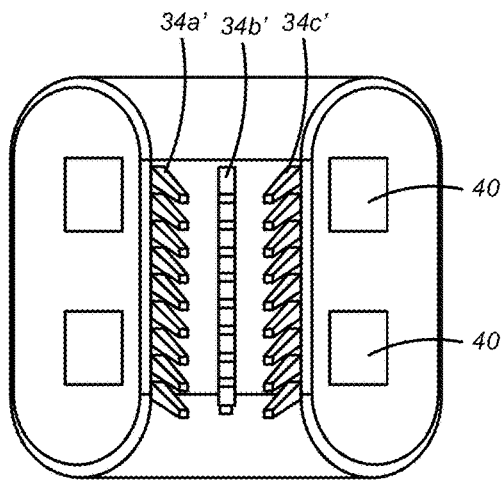
Figure 16C:
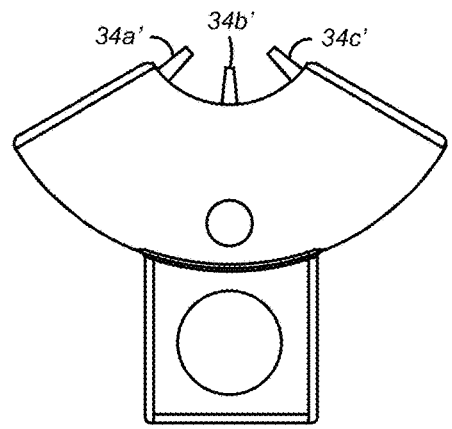
Figure 16D:
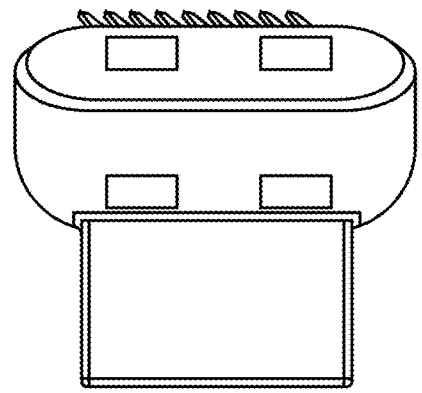

In a non-lengthening context, the device also allows the distribution of loads across the clamp, as opposed to across sutures, to protect tissue from physiological or non-physiological movement. This implementation is similar to that of the schematic diagram of FIG. 1B. In an exemplary procedure, and referring to FIG. 15, devices (left set of arrows) were deployed on proximal and distal nerve stumps of a 3 mm rat sciatic nerve gap. Nerve gripping enabled a tension-free repair of the nerve with 3 10-0 sutures. The repair in the presence of devices remained intact even when the knee was maximally extended and ankle dorsiflexed, a joint configuration which imposes maximum strain (deformation) on the sciatic nerve and which damaged the nerve and/or pulled out sutures in the absence of device implantation. This example shows the utility of the assembly of devices even in the case where sequential and extended nerve elongation is not the goal. In the example of FIG. 15, the nerve ends were immediately brought together and sutured. However, in the absence of the tissue gripping devices, if maximal extension occurred, the sutures would generally not be enough to hold the nerve endings together, as the junction is the weakest point of the nerve. The two devices thereby provided a strain relief structure that allowed the nerve endings to grow together, while still being embodied in an implantable device with a footprint small enough to allow implantation into a host. In this case, the devices may be left in the body, the devices may be made biodegradable, and so on.

In a related variation, a guide rod may be secured between the tissue gripping devices, even if the two tissue gripping devices are not brought completely together, so as to maintain a fixed position and orientation between the two secured tissues.

Variations

Given the above description, numerous variations will be understood.

For example, referring to FIGS. 16A-16D, an alternative implementation of a device 50' is shown with a significantly smaller footprint, as may be employed to secure smaller tissues, or where lesser force is needed. Such a device has been shown to effectively secure tissue in nerves of rats. As may be seen, only two suture holes 40 are provided, giving the device a significantly smaller footprint. Such devices are particularly minimally invasive, and may be effectively employed in which devices need to be deployed in very small spaces, including pediatric applications. Barbs 34a', 34b', and 34c' are also shown. It is a prototype of the device of FIG. 16 that is shown in FIG. 15.

The above description illustrates various exemplary implementations and embodiments of the systems and methods according to present principles. The invention is not limited to such examples. The scope of the invention is to be limited only by the claims appended hereto, and equivalents thereof.

The invention claimed is:

1. An implantable device operable to grip a nerve, comprising:
   a. a housing;
   b. a device connection portion coupled to or defined within the housing; and
   c. a tissue engagement portion attached to or defined in the housing, the tissue engagement portion including a tissue engagement surface, the tissue engagement surface having at least one tissue piercing element thereon, the tissue piercing element operable to hold tissue against movement, wherein the tissue is a nerve and the piercing element is a micro-barb having a depth that is operable to engage only an epineurium of a nerve, such that damage to the inner nerve is prevented,
   d. wherein the housing, the device connection portion, and the tissue engagement portion are configured to fit and be implanted within a host, and wherein the tissue engagement portion is configured to distribute a radial compressive load along the nerve.

2. The device of claim 1, wherein the device connection portion defines a connection throughhole, the connection throughhole having a cylindrical shape.

3. The device of claim 2, wherein the connection throughhole is operable to receive a tube.

4. The device of claim 3, wherein the tube is a hypotube.

5. The device of claim 4, wherein the connection throughhole is operable to receive a backbone through the hypotube.

6. The device of claim 4, wherein the hypotube is secured in the connection throughhole by a friction fit.

7. The device of claim 2, wherein the connection throughhole is operable to receive a backbone.

8. The device of claim 7, wherein the backbone defines a slot operable to receive a guidewire.

9. The device of claim 2, wherein the housing further defines a guidewire hole, the guidewire hole having a cylindrical shape, and wherein an axis of the cylindrical shape of the guidewire hole is substantially parallel to an axis of the cylindrical shape of the connection throughhole.

10. The device of claim 1, wherein the tissue engagement portion further includes at least one suture throughhole, the suture throughhole operable to allow an operator to suture or strap a subject tissue to the tissue engagement surface.

11. The device of claim 1, wherein the tissue engagement portion further includes a top housing portion and a bottom housing portion, the top housing portion coupled to the bottom housing portion by a tightenable connector, a volume between the top housing portion and the bottom housing portion defining a receiving volume operable to receive tissue to be gripped, and wherein the at least one tissue piercing element is situated to extend into the receiving volume.

12. The device of claim 1, wherein the device connection portion and the tissue engagement portion are on opposite sides of the housing.

13. The device of claim 1, wherein the micro-barb has an angle of between 40 and 50 degrees to the housing.

14. A kit for elongating tissue, comprising:
   a. at least two devices according to claim 1;
   b. a backbone operable to connect the at least two devices and to maintain the at least two devices in sliding engagement; and
   c. a means to maintain the at least two devices at a maximum distance.

15. The kit according to claim 14, wherein the means to maintain includes a guidewire.

16. The kit according to claim 15, wherein the means to maintain includes a set screw operable to hold each of the respective devices against movement relative to the guidewire.

17. The kit according to claim 15, wherein the means to maintain includes a tie off hitch operable to hold each of the respective devices against movement relative to the guidewire.

18. The kit according to claim 15, wherein the elements of the kit are configured to fit and be implanted within a host.

19. The kit according to claim 14, further comprising a ratchet configured to move the two devices in a direction towards each other.

20. A method for elongating a tissue, or to bring to disparate tissues together, comprising:
   a. attaching a first device according to claim 1 to a proximal portion of tissue;
   b. attaching a second device according to claim 1 to a distal portion of tissue;
   c. affixing a backbone between the first and second devices, such that a distance between the proximal portion of tissue and the distal portion of tissue is maintained; and
   d. successively altering the position of the first or second device, or both, on the backbone, such that the distance is reduced with each successive altering.

21. The method of claim 20, wherein the affixing a backbone such that a distance is maintained is performed by maintaining a maximum distance between the proximal portion of tissue and the distal portion of tissue.

* * * * *